(12) United States Patent
Trigiante

(10) Patent No.: US 8,410,125 B2
(45) Date of Patent: Apr. 2, 2013

(54) SULFONATED PRECURSORS OF THYMIDINE FOR THE TREATMENT OF EPITHELIAL HYPERPLASIAS

(75) Inventor: Giuseppe Trigiante, London (GB)

(73) Assignee: Yagna Limited, London (GB)

( * ) Notice: Subject to any disclaimer, the term of this patent is extended or adjusted under 35 U.S.C. 154(b) by 279 days.

(21) Appl. No.: 12/741,419

(22) PCT Filed: Nov. 5, 2008

(86) PCT No.: PCT/GB2008/003727
§ 371 (c)(1),
(2), (4) Date: May 5, 2010

(87) PCT Pub. No.: WO2009/060186
PCT Pub. Date: May 14, 2009

(65) Prior Publication Data
US 2011/0053965 A1    Mar. 3, 2011

Related U.S. Application Data

(60) Provisional application No. 60/985,496, filed on Nov. 5, 2007.

(51) Int. Cl.
*A61K 31/505* (2006.01)
(52) U.S. Cl. ..................................................... 514/274
(58) Field of Classification Search .................... 514/274
See application file for complete search history.

(56) References Cited

U.S. PATENT DOCUMENTS

2003/0027833 A1 *   2/2003   Cleary et al. ................. 514/270

FOREIGN PATENT DOCUMENTS

| WO | 00/67759 | 11/2000 |
| WO | 2006/073359 | 7/2006 |
| WO | 2007/083173 | 7/2007 |

OTHER PUBLICATIONS

Melvin et al. (Eur. J. Biochem 92; 373-379 (1978).*
Choi et al. "Some General Influences on N-Decylmethyl Sulfoxide on the Permeation of Drugs Across Hairless Mouse Skin." J. Invest. Dermatol. 96(6): 822-826, 1991.
Massey et al. "Photoactivation of DNA Thiobases as a Potential Novel Therapeutic Option." Current Biology, 11(14): 1142-1146, Jul. 24, 2001.
Salet et al. "4-Thiouridine as a Photodynamic Agent." Photochemistry and Photobiology, 41(5): 617-619, 1985.
Ziolowski et al. "Pretreatment of Plantar Warts with Azone Enhances the Effect of 5-Aminolevulinic Acid Photodynamic Therapy." J. Environ. Pathol. Toxicol. Oncol. 25(1-2): 403-409, 2006.
International Search Report from PCT/GB2008/003727, Dec. 2, 2009.

* cited by examiner

*Primary Examiner* — Shirley V Gembeh
(74) *Attorney, Agent, or Firm* — MDIP LLC

(57) ABSTRACT

This invention relates to pharmaceutical compositions comprising a sulfonated biological precursor of thymidine, such as a precursor of 4-thiothymidine (4-TT), and their use in the photodynamic treatment of skin hyperplasias, including cancer, psoriasis, actinic keratosis and keloids, by topical or systemic administration.

14 Claims, 3 Drawing Sheets

Thymidine (T)

4-Thiothymidine (4-TT)

4-Thioorotate and its 6 position esters

SULFONATED PRECURSORS OF THYMIDINE FOR THE TREATMENT OF EPITHELIAL HYPERPLASIAS

CROSS REFERENCE TO RELATED APPLICATIONS

This application is a 371 national stage application of International Application No. PCT/GB2008/003727, filed Nov. 5, 2008, which claims priority to U.S. Application No. 60/985, 496, filed Nov. 5, 2007, which is incorporated by reference in its entirety.

FIELD OF THE INVENTION

The invention pertains to the photodynamic treatment of skin hyperplasias including cancer, psoriasis, actinic keratosis and the like, using precursor molecules of 4-thiothymidine (4-TT) for topical and systemic application.

BACKGROUND OF THE INVENTION

Epithelial cancers are the most common ones. They all stem from a hypertrophic growth of cells making up the epithelia, or linings, of internal organs, and the skin. These include skin, lung, stomach, colon and bladder cancer.

Skin cancers in their various forms account for the most frequent cancers. Only one of them, melanoma, is seriously life threatening. Non-melanoma cancers such as basal cell carcinomas (BCC) although very common are relatively benign; squamous cell carcinomas (SCC) are intermediate in danger because they can occasionally metastasise. Hyperplasias such as actinic keratosis (AK) are so called precancerous lesions because they can lead to SCC if left untreated.

Apart from these, there are other conditions that are not life threatening but are the cause of much distress for the patient and require treatment. Psoriasis is an autoimmune disease which results in chronic inflammation of patches of skin causing itching and pain. Keloids are instead abnormal scars which grow to many times the size of the original wound on susceptible individuals. The main treatment is surgical removal but this unavoidably results in another wound with a 50% chance of the keloid returning. A non invasive treatment would be most needed.

With the exception of melanoma, all these conditions affect the outer layers of the skin (epidermis) and are therefore amenable to topical cures as their modest thickness allows access to skin penetrating formulations.

Internal cancers such as lung and the digestive tract (stomach/colon) both represent major causes of mortality and a significant percentage of all cancer deaths. Even though modern preventive approaches have succeeded in reducing incidence, on the therapy side little has been done in terms of specificity of treatment, i.e. non-chemotherapeutic approaches. These cancers all present an interface to air, which makes them potentially accessible to a light emitting probe and therefore to photodynamic therapy.

Photodynamic therapy (PDT) is a novel treatment for hyperproliferative diseases of the skin and internal epithelia. It involves the administration, topical or systemic, of a photosensitive agent which will ideally concentrate in the proliferating tissues of the body. The compound itself is inactive but upon irradiation with a light of a specific wavelength the molecule is chemically activated and stimulated to undergo chemical reactions which either damage the cell directly or result in the production of species that in turn destroy the cells. This way the chemotherapeutic action is physically confined to an area of interest instead of extending to the whole body of the patient with unpleasant and harmful side effects. The field of applicability of photodynamic therapy is naturally limited by the accessibility of tissue to the light source.

Current agents for photodynamic therapy are mainly based on the porphyrin molecule, a derivative of haemoglobin. This molecule absorbs light in the red region of the spectrum and, as a result, is excited into a chemically reactive singlet state. It subsequently releases this energy to molecular oxygen, abundant in cells, turning it into the reactive singlet oxygen molecule. Singlet oxygen in turn causes widespread damage to cellular biomolecules, resulting in cell death.

The compounds in the PDT field today are porphymer sodium (PHOTOPRIN™) and 5-aminolevulinic acid (ALA). PHOTOPRIN™ is a porphyrin derivative which has been licensed for systemic use in the United States and Europe for the treatment of bronchial, lung, bladder and oesophageal cancer. ALA instead is a porphyrin precursor which is converted into protoporphyrin IX directly in cells; it is administered topically and it is licensed for the treatment of actinic keratosis. Its mode of administration involves applying the emulsion on the affected area, then following 14 hours irradiate with red light. An ALA derivative, methyl aminolevulinate (MAL) has been developed and, under the trade name METVIX™, is in use for pre-malignant conditions of the skin (such as basal cell carcinomas and actinic keratosis).

A major disadvantage of the systemic approach (such as PHOTOPRIN™) is the slow clearance of the drug which means that patients cannot be exposed to sunlight or strong lights for many days after treatment. Due to the nature of the molecules themselves, they do not play a biological role in cells. Thus, the molecules do not have the ability to target the proliferating cells as desired.

Recently, a new approach to photodynamic therapy has been introduced. In a recent literature reference, the molecule 4-thiothymidine (4-TT) was described (see Karran P. et al., "Photoactivation of DNA thiobases as a potential novel therapeutic option", Current Biology, 11(14), 1142-6 (2001)). This molecule is a derivative of thymidine. Thymidine is a pyrimidine nucleotide, one of the four building monomers of DNA. As such, it is needed by all cells in a state of proliferation in order to replicate their DNA. Upon exposure to UV-B, the harmful form of ultraviolet radiation, thymidine undergoes a photochemical reaction which leads to its dimerization to form thymidine dimers, a potentially DNA damaging species. This is why the skin needs protection from UV-B, which is present in small amounts in sunlight. On the contrary, the UV-A fraction of sunlight is harmless to thymidine and DNA. 4-thiothymidine (4-TT) shares with its parent nucleotide the ability to concentrate in proliferating cells but not in normal tissue. Besides, it has the remarkable distinction to be able to absorb in the near UV (UV-A), a region of the spectrum which is quite harmless to normal DNA and cells, and to chemically react with and damage the surrounding DNA once exposed to said radiation. It is foreseen therefore that the species would concentrate in the cells making up the hyperproliferative lesion but not in the surrounding normal tissue. The subsequent irradiation of said tissue with UV-A light ensures that only those cells responsible for the hyperplasia would be targeted and killed.

Research by Karran P. et al. has illustrated the potential for the use of a novel thymidine derivative, 4-thiothymidine (4-TT), in the fight against cancer. This modified thymidine molecule displays a shift in its absorbance peak from 260 nm (UV-B) to 335 nm (UV-A). Excitation of the cells containing 4-thiothymidine (4-TT) at this wavelength will cause the cells to undergo a photochemical reaction producing toxicity in the cells. This modified molecule is an excellent candidate for photodynamic therapy, particularly with its ability as a nucleotide to concentrate in proliferating cells' DNA which provides it with an advantage over other PDT drugs. In fact, since the skin is the only area where the patients will be exposed to ambient light, no significant amount of 4-thiothymidine (4-TT) will be accumulated after treatment because the skin is not hyperproliferative. Moreover, the fact that UV-A radiation is less common than red light and requires direct exposure to sunlight, makes the issue of side effects and patient protection even less relevant. The precautions associated with the use of PHOTOPRIN™ would therefore ideally not be applicable to this new drug.

The employment of nucleotide analogs for the treatment of disease is established in medical practice and particularly in cancer research. Drugs such as fluorouracil and cytarabine are already in use in chemotherapy. Sulfo derivatives of nucleotides are also already known in the art, for example, Azathioprim (IMURAN™) is in use as an antimetabolite for immunosuppression. This molecule is however a nucleotide analog toxic on its own account and does not require photoactivation. The novelty brought about by the 4-TT molecule is in that it is technically a prodrug. Its metabolism, DNA incorporation and base pairing are compatible with its natural analog thymidine and so it is not initially toxic like the other molecules mentioned above. Its toxicity is only revealed following UV irradiation and only where this irradiation occurs.

It is therefore an object of the present invention to provide compositions comprising certain compounds which are biological precursors of thymidine, especially precursors of 4-TT, and which can be used in the photodynamic treatment of skin and internal epithelia hyperplasias. Such compounds are termed "biological precursors" since, once delivered, they are metabolised by normal physiological pathways to form the active molecule.

SUMMARY OF THE INVENTION

One embodiment of the invention encompasses a formulation for treating skin and internal epithelia hyperplasias comprising a precursor molecule of 4-TT and at least one penetration enhancer. The precursor molecule may be 4-thiodihydroorotate, 4-thioorotate, 4-thioorotidylate and 4-thiouridylate or any sulfur containing compound of precursors of 4-thiothymidine (4-TT). The penetration enhancer may be an alcohol (eg. ethanol), a sulfoxide (eg. DMSO), a hydroxylated polymers (eg. polyethylene glycol) or a naturally derived microfibrillated polysaccharide (eg. microfibrillated cellulose or microfibrillated starch), as well as a cyclodextrin.

Another embodiment of the invention encompasses a method for treating skin and internal epithelia hyperplasias comprising applying a formulation to a lesion area on a patient, in a topical or systemic manner. The lesion area may be pre-treated with solvents and moisturizers of specific wetting compounds to facilitate subsequent penetration of the applied formulation. The formulation can be applied directly, or through the use of an occlusive dressing or in the form of a patch. A lag time follows after application of the formulation and the lesion area is then irradiated with UV-A light in a sufficient intensity and time duration to cause photochemical reaction of the drug and death by apoptosis or necrosis of the affected cells. The treatment can then be repeated, with or without renewed drug administration, for the required period to experience benefits.

DETAILED DESCRIPTION OF THE INVENTION

Figure 1:
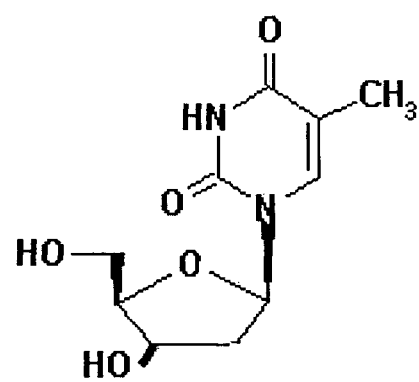
FIG. 1 illustrates the structures for thymidine (T) and 4-thiothymidine (4-TT).
Figure 1:
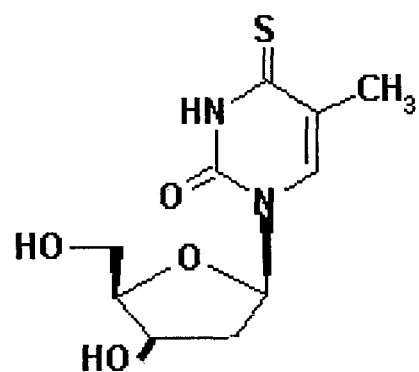

The invention encompasses the use of a precursor molecule for the purpose of photodynamic treatment of skin hyperplasias. The precursor molecules are biological precursors of 4-thiothymidine (4-TT), which is a derivative of the nucleotide thymidine, present in DNA. The structures of thymidine (T) and 4-thiothymidine (4-TT) are shown in FIG. 1.

Whereas 4-TT is the final nucleotide in the thymidine synthesis pathway, there are a number of compounds which lie upstream of it in the pathway which leads to biosynthesis of thymidine. All of those precursors can be conveniently modified as to include the sulfur atom in the 4-carbonyl position which will eventually become number 4 on the pyrimidine ring and therefore lead to 4-TT as the ultimate product.

The use of such compounds as opposed to 4-TT itself has multiple advantages. First, the precursors are smaller and easier to synthesise. Secondly, their dimensions allow them to better distribute in the tissues and penetrate epithelia and cellular barriers therefore aiding drug pharmacokinetics. As an added advantage, the molecules in question can be further derivatised in order to specifically target them to tissues and organs.

Figure 3:
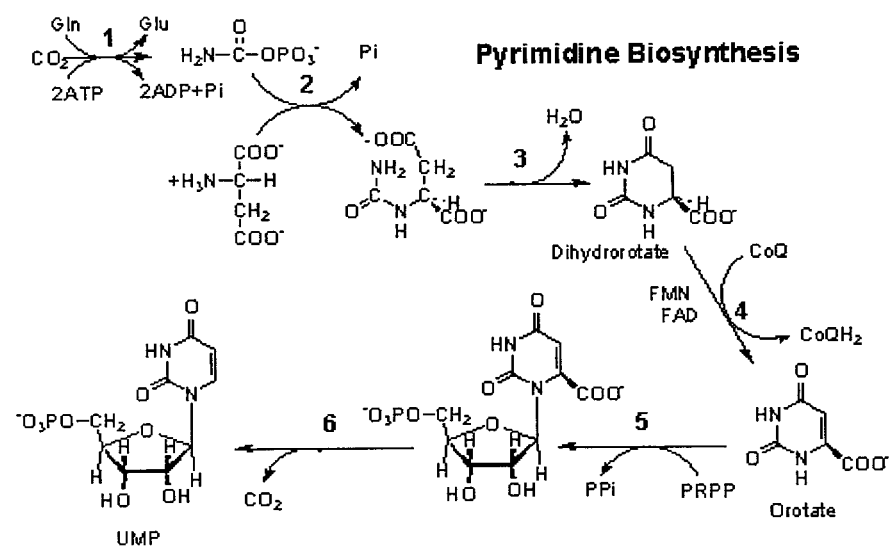
FIG. 3 illustrates the metabolic pathway for the de novo synthesis of thymidine.

The metabolic pathway for the de novo synthesis of thymidine is shown in FIG. 3. Carbamoyl phosphate is fused to aspartate to form carbamoyl aspartate. This is then annulated to form dihydroorotate. The latter is dehydrogenated to form orotate, which is then inserted onto a ribose ring to form orotidylate. Finally, orotidylate is decarboxylated to form uridylate or UMP, which is then methylated to form thymidine.

There are many intermediates along this synthetic pathway but it is evident that the carboxyl group of aspartate is the direct precursor of the 4-carbonyl of orotidylate and thymidine. Replacement of 4-carbonyl with sulfur should result in the cell producing 4-thiothymidine as the end product instead of thymidine. This can also occur at the other stages in the synthesis, i.e. dihydroorotate, orotate, orotidylate or uridylate. Typically the precursor molecules are 4-thiodihydroorotate, 4-thioorotate, 4-thioorotidylate, 4-thiouridylate or any sulfur containing compound of precursors of 4-thiothymidine (4-TT).

This method provides a practical way of exploiting the cell's own machinery to produce a photodynamic therapy drug starting from a simpler molecule. It is this realization which lies at the base of the invention. We envisage that delivering thioorotate or any of the above mentioned analogs to the target cell could result in the in situ production of thiothymidine, its incorporation in DNA and the sensitisation of the cell to UV-A light.

Additionally, to increase efficacy, the precursor molecules in question can be further modified at their 6-position, i.e. the 6-position of the pyrimidine ring, as the carboxylic moiety of orotic acid lends itself to esterification with suitable molecules endowed with a hydroxyl moiety. (See FIG. 2). Alcohols can be chosen so as to provide the molecule with any desired physical and chemical characteristics such as modified lipophilicity, increased affinity to cell membranes, and specific tissue targeting. Once inside the target cell, the ester will be cleaved by cellular non-specific esterases into the active molecule itself which will be metabolised as described above to 4-TT.

Figure 2:
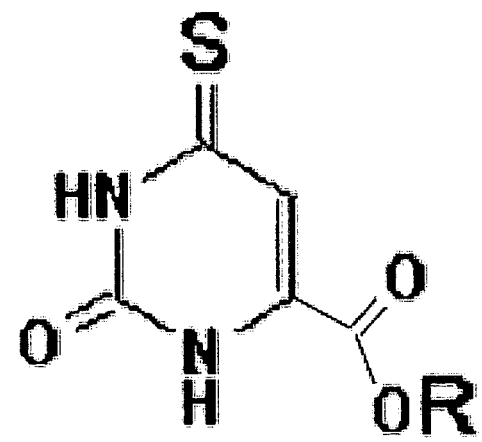
FIG. 2 illustrates the structure for 4-thioorotate showing an ester group at the 6-position.

R in the formula of FIG. 2 may represent a hydrogen atom or an optionally substituted alkyl group. Any alkyl group, unless otherwise specified, may be linear or branched and may contain up to 12, preferably up to 8, more preferably up to 6, and especially up to 4 carbon atoms. Preferred alkyl groups are methyl, ethyl, propyl and butyl.

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano, hydroxyl, cycloalkyl, alkyl, alkenyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, alkylsulphonato, arylsulphinyl, arylsulphonyl, arylsulphonato, carbamoyl, alkylamido, aryl and aralkyl groups.

When any of the foregoing optional substituents represents or contains an alkyl or alkenyl substituent group, this may be linear or branched and may contain up to 12, preferably up to 8, more preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A halogen atom may be a fluorine, chlorine, bromine or iodine atom and any group which contains a halo moiety, such as a haloalkyl group, may thus contain any one or more of these halogen atoms.

Preferred optional substituents include halogen atoms, nitro, cyano, hydroxyl, $C_{1-6}$ alkyl, $C_{1-6}$ haloalkyl, $C_{1-6}$ alkoxy, $C_{1-6}$ haloalkoxy, amino, $C_{1-6}$ alkylamino, di-($C_{1-6}$ alkyl) amino, formyl, $C_{1-6}$ alkoxycarbonyl, carboxyl, $C_{1-6}$ alkanoyl, $C_{1-6}$ alkylthio, $C_{1-6}$ alkylsulphinyl, $C_{1-6}$ alkylsulphonyl, carbamoyl and $C_{1-6}$ alkylamido groups. Particularly preferred optional substituents include halogen atoms, nitro, cyano, hydroxyl, $C_{1-4}$ alkyl, $C_{1-4}$ haloalkyl, $C_{1-4}$ alkoxy and $C_{1-4}$ haloalkoxy groups with halogen atoms being especially preferred.

The precursor molecules described can be administered in three major ways: orally, intravenously or topically. This is because the essence of photodynamic therapy, i.e. the selective activation of the compounds by UV-A light, allows the systemic distribution of the molecules without any side effects except in the area where light is then applied.

The invention therefore also provides a pharmaceutical composition which comprises a carrier and, as active ingredient, a sulfonated biological precursor of thymidine, such as a precursor of 4-thiothymidine. A process for the preparation of a pharmaceutical composition as defined above is also provided which comprises bringing a sulfonated biological precursor of thymidine, such as a precursor of 4-thiothymidine, into association with a carrier.

A pharmaceutically acceptable carrier may be any material with which the active ingredient is formulated to facilitate administration. A carrier may be a solid or a liquid, including a material which is normally gaseous but which has been compressed to form a liquid, and any of the carriers normally used in formulating pharmaceutical compositions may be used. Preferably, compositions according to the invention contain 0.00001% to 1% by weight of active ingredient.

The precursor molecules can be formulated as, for example, tablets, capsules, suppositories or solutions. These formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as *acacia*, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-*acacia* complexes; sugars such as mannitol, dextrose, galactose and trehalose; cyclic sugars such as cyclodextrin; inorganic salts such as sodium phosphate, sodium chloride and aluminum silicates; and amino acids having from 2 to 12 carbon atoms such as a glycine, L-alanine, L-aspartic acid, L-glutamic acid, L-hydroxyproline, L-isoleucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include sodium hydrogencarbonate, citric acid, tartaric acid, phosphoric acid, hydrochloric acid and maleic acid. Suitable sweeteners include aspartame, acesulfame K and thaumatin. Suitable taste-masking agents include sodium hydrogencarbonate, ion-exchange resins, cyclodextrin inclusion compounds, adsorbates or microencapsulated actives.

In the case of topical application, the drug will be administered to the patient's lesion area locally by means of a skin penetrating formulation. All human epithelia, and the skin in particular, exhibit some kind of barrier effect to prevent indiscriminate crossing of compounds. The skin is particularly apt to this purpose by means of the so called cornified layer which is the thin but very impermeable outermost coating of the skin, made of dead cells cemented together by keratins and lipids. Crossing this barrier for the purpose of drug delivery is a formidable challenge. A considerable amount of knowledge exists in the art concerning manners to overcome the cornified layer barrier. For example, it has been observed that pretreatment of the skin with solvents, moisturizers of specific wetting compounds (i.e. acetone, AZONE™, dimethylsulfoxide, 1-methyl-2-pyrrolidone, decylmethyl sulfoxide, or polyethylene glycol) facilitates subsequent penetration of applied formulations. The same compounds may be used within the formulation for the same purpose. The composition for this purpose can be formulated conventionally with one or more physiologically acceptable thickeners, carriers or excipients, according to techniques known in the art, such as gels, creams, ointments, sprays, lotions, soaps, and any of the other conventional pharmaceutical vehicles for topical transdermal delivery. The drug concentration in the formulation is variable but generally present in an amount of about 1 µM to 1 mM (0.000018% to 0.018% w/w). Its low molecular weight (less than one third that of PHOTOPRIN™) is predictive of a higher penetration efficiency. Among the penetration enhancers that could be included in the formulation itself are alcohols (eg. ethanol), sulfoxides (eg. DMSO), hydroxylated polymers (eg. polyethylene glycol) and the naturally derived microfibrillated polysaccharides (eg. microfibrillated cellulose or microfibrillated starch), as well as cyclodextrins. Also, the use of physical enhancers such as iontophoresis and abrasion is feasible to increase penetration efficiency. Typically, the penetration enhancer is present in an amount of about 1% to 80% by weight of the formulation.

Prior to the application of the formulation the skin may be treated with compounds which are known to facilitate subsequent skin penetration of formulations such as AZONE™ (Ziolkowski P. et al., "Pretreatment of plantar warts with azone enhances the effect of 5-aminolevulinic acid photodynamic therapy", *J. Environ Pathol Toxicol Oncol.*, 25(1-2), 403-9 (2006)), or decylmethyl sulphoxide (Choi H-K et al., "Some general influences of n-decylmethyl sulfoxide on the permeation of drugs across hairless mouse skin", *J. Invest Dermatol.*, 96(6), 822-6 (1991)).

The formulation itself can be applied directly, through the use of an occlusive dressing or in the form of a patch.

In the case of systemic delivery, the composition can be injected, taken orally or parenterally or by any known method of administration. It is envisaged that the preferred dosage would be between 2 and 200 mg/kg body weight.

Following application, a lag time must take place to ensure the drug is fully incorporated into cells and their DNA. Typically, the lag time is between 12 to 48 hours. Following this lag time, a UV-A radiation is applied, preferably about 1 $kJ/m^2$ to 50 $kJ/m^2$. For this purpose any suitable UV-visible light source may be used with emission spectra between 300 nm to 600 nm. No emission spectra under 300 nm should be applied because it contains the harmful UV-B radiation. The radiation source can be diverse, for example, lamps for external epithelia or light emitting probes and fibre optic for internal use directing towards bladder, colon and lung cancer. The cells nearest the epithelia will be most affected and are expected to die of cellular apoptosis within 24 hours. Since the depth of drug penetration and incorporation is expected to exceed that of UV radiation penetration, one round of irradiation will probably not cover the whole lesion and therefore repeated applications are allowed. These are made possible by the known safety of UV-A radiation.

This formulation can be applied to all areas of the body, external and internal, which are in principle accessible to a light emitting probe. This includes all of the skin surface plus the mouth, neck, oesophagus, stomach and intestine, as well as part of the bronchial system, especially the lungs, and the bladder. It is understood that the amount of the formulation used and the intensity and time duration of UV radiation applied to a lesion area will vary depending upon a patient's age, weight, types of lesion and size of the lesion or tumour targeted. The treatment is considered complete when all affected cells in the lesion area have been destroyed.

In the case of the digestive tract the employment of photodynamic therapy is all the more desirable since classical chemotherapy cannot be administered topically as some absorption through the walls of the intestine is unavoidable. Particularly, in the case of the mouth the constant flux of saliva would rapidly cause ingestion and absorption in the bloodstream of any classical chemotherapeutic.

The compositions of the invention, especially those described in the examples, are preferably aimed at topical delivery of the drug.

Having described the invention with reference to certain preferred embodiments, other embodiments will become apparent to one skilled in the art from consideration of the specification. The invention is further defined by reference to the following examples describing in detail the photodynamic treatment of skin hyperplasias including cancer, psoriasis, actinic keratosis and the like, using a formulation comprising a precursor molecule and a penetration enhancer for topical and systemic application. It will be apparent to those skilled in the art that many modifications, both to materials and methods, may be practiced without departing from the scope of the invention.

EXAMPLES

Example 1

A stage 1 bladder cancer patient is treated with 1 mg/mL 4-thioorotate intravenously for 24 hours. Following this 24 hour period, a cystoscopic probe is inserted in the urethra and into the bladder. By means of fibre optic UV-A light is shone onto the bladder lesion. The treatment is repeated twice a week and tumour regression monitored by cystoscopy.

Example 2

A patient suffering from a BCC (basal cell carcinoma) lesion on the arm is treated in the following way. The lesion is cleaned, then pre-treated with acetone and DMSO for 10 min. Following this a gel consisting of 10 μM 4-thioorotate octyl ester, 40% DMSO in saline buffer and 2% microfibrillated cellulose is applied to the lesion. The lesion is dressed with surgical membrane and left untouched for 4 hours. After this period the dressing is removed and the lesion cleaned and dressed normally. 20 hours later the lesion is irradiated with a UV-A lamp with an emission of 350 nm, for a period of 10 minutes and a total energy of 10 $kJ/m^2$ is applied. The irradiation is repeated for a period of one week, following which the whole treatment is repeated three times. Regression of the BCC is then assessed by biopsy and photography.

Example 3

A patient suffering from psoriasis has the lesion directly covered with a solution of 50 μM 4-thioorotate in 20% DMSO, 10% PEG and 70% HEPES buffer. The lesion is dressed and the solution is re-applied to the lesion after four hours, and once more after that. In the following day, 24 hours after the last application, UV-A light is shone on the lesion with an emission of 350 nm, for a period of 20 min, and a total energy of 20 $kJ/m^2$ is applied. The irradiation is repeated for 20 days and regression of the lesion monitored photographically.

Example 4

A stage 1 bladder cancer patient is treated with 20 mg/kg 4-thioorotate intravenously for 24 hours. Following this 24 hour period, a cystoscopic probe is inserted in the urethra and into the bladder. By means of fibre optic UV-A light is shone onto the bladder lesion. The treatment is repeated twice a week and tumour regression monitored by cystoscopy.

Further aspects of the invention include:

Aspect 1 A method for treating skin and internal epithelia hyperplasias, the method consisting of administering a 4-thio thymidine releasing composition to the patient, in a topical or systemic manner, for one or more times and subsequently exposing the lesion to UV-A light to activate the photosensitizer.

Aspect 2 The method of aspect 1 in which the photosensitizer releaser in the composition is a sulfonated biological precursor of thymidine, i.e. a precursor of 4-thio thymidine.

Aspect 3 The method of aspect 2 in which the precursor is one of: 4-thioorotate, 4-thiodihydroorotate, 4-thiouridylate, carbamoyl-thioaspartate.

Aspect 4 The method of aspect 3 in which the thioorotate molecule is further derivatized at the 6 carboxylic position into an ester with an alcohol.

Aspect 5 The method of aspect 4 in which the alcohol is a compound designed to facilitate penetration of skin and cell membranes.

Aspect 6 The method of aspect 1 where the UV-A irradiation has a wavelength comprising the absorption peak of the photosensitizer and is comprised between 300 and 600 nm Aspect 7 The method of aspect 1 where the cellular death is caused by apoptosis or necrosis.

Aspect 8 The method of aspect 1 where the hyperplasia is one of: skin, head and neck, stomach, lung, colon and bladder cancer, psoriasis, actinic keratosis and keloids, Aspect 9 The composition of aspect 1 where the composition is applied topically in a formulation containing a penetration enhancer.

Aspect 10 The composition of aspect 9 where the penetration enhancer is a sulfoxide (dimthylsulfoxide, decylmethylsulfoxide, dimethylsulfoacetamide and the like).

Aspect 11 The composition of aspect 9 where the penetration enhancer is an alcohol.

Aspect 12 The composition of aspect 9 where the penetration enhancer is a hydroxylated polymer (polyethylene glycol, polypropylene glycol ad the like).

Aspect 13 The composition of aspect 9 where the penetration enhancer is a natural microfibrillated polysaccharide (micrifibrillated cellulose, microfibrillated starch, microfibrillated dextran, cyclodextrins).

Aspect 14 The method of aspect 1 where the UV-A irradiation is repeated several times in the period following a single application of the chemical.

The invention claimed is:

1. A pharmaceutical composition comprising a sulfonated de novo synthesis precursor of thymidine and a carrier, wherein the sulfonated de novo synthesis precursor of thymidine is a precursor of 4-thiothymidine.

2. The composition according to claim 1, wherein the sulfonated de novo synthesis precursor of 4-thiothymidine is selected from the group consisting of 4-thioorotate, 4-thiodihydroorotate, 4-thiomidylate, and carbamoyl-thioaspartate.

3. The composition according to claim 2, wherein the sulfonated de novo synthesis precursor is further derivatised at the 6 carboxylic position into an ester by reaction with an alcohol.

4. The composition according to claim 3, wherein the alcohol is a compound designed to facilitate penetration of skin and cell membranes.

5. The composition according to claim 1, wherein the composition is formulated for topical administration.

6. The composition according to claim 5 further contains a penetration enhancer.

7. The composition according to claim 6, wherein the penetration enhancer is an alcohol.

8. The composition according to claim 6, wherein the penetration enhancer is a hydroxylated polymer.

9. The composition according to claim 8, wherein the hydroxylated polymer is polyethylene glycol or polypropylene glycol.

10. The composition according to claim 6, wherein the penetration enhancer is a natural microfibrillated polysaccharide.

11. The composition according to claim 10, wherein the natural microfibrillated polysaccharide is selected from the group consisting of microfibrillated cellulose, microfibrillated starch, microfibrillated dextran and cyclodextrins.

12. The composition according to claim 6, wherein the penetration enhancer is a sulfoxide.

13. The composition according to claim 12, wherein the sulfoxide is selected from the group consisting of dimethylsulfoxide, decylmethylsulfoxide and dimethylsulfoacetamide.

14. The composition according claim 1, further comprising a pharmaceutically acceptable carrier.

* * * * *